(12) United States Patent
Farber (10) Patent No.: US 9,304,101 B1
(45) Date of Patent: Apr. 5, 2016

(54) METHOD OF SENSOR CONDITIONING FOR IMPROVING SIGNAL OUTPUT STABILITY FOR MIXED GAS MEASUREMENTS

(71) Applicant: Boris Farber, Solon, OH (US)

(72) Inventor: Boris Farber, Solon, OH (US)

(73) Assignee: BJR SENSORS LLC, Solon, OH (US)

( * ) Notice: Subject to any disclaimer, the term of this patent is extended or adjusted under 35 U.S.C. 154(b) by 632 days.

(21) Appl. No.: 13/648,417

(22) Filed: Oct. 10, 2012

Related U.S. Application Data (63) Continuation-in-part of application No. 11/152,971, filed on Jun. 15, 2005, now Pat. No. 7,585,402.

(60) Provisional application No. 61/545,613, filed on Oct. 11, 2011, provisional application No. 60/580,606, filed on Jun. 18, 2004, provisional application No. 60/599,513, filed on Aug. 9, 2004.

(51) Int. Cl.
*G01N 27/407* (2006.01)
*G01N 27/406* (2006.01)

(52) U.S. Cl.
CPC ...... *G01N 27/4067* (2013.01); *F01N 2560/026* (2013.01)

(58) Field of Classification Search
CPC ............. G08B 17/117; G01N 27/4067; F01N 2560/20; F01N 2560/026
See application file for complete search history.

(56) References Cited

U.S. PATENT DOCUMENTS

| 4,510,036 | A  | * | 4/1985 | Takeuchi et al. | ............... | 204/425 |
| 6,341,599 | B1 | * | 1/2002 | Hada et al. | ..................... | 123/688 |
| 7,585,402 | B2 | * | 9/2009 | Farber | ........................ | 205/784.5 |

FOREIGN PATENT DOCUMENTS

DE        3634786 A1 *  4/1988   ............ G01N 27/12

OTHER PUBLICATIONS

EPO machine-generated English language translation of H. Rump DE 3634786 A, patent published Apr. 14, 1988.*
Derwent English language Abstract of H. Rump DE 3634786 A, patetn published Apr. 14, 1988.*
Article entitled "What is the difference between resistance and impedance?" downloaded from PhysLink.com on Mar. 4, 2015.*

* cited by examiner

*Primary Examiner* — Alexander Noguerola
(74) *Attorney, Agent, or Firm* — John D. Gugliotta

(57) ABSTRACT

An improved pulse discharge technique is provided which continuously measures a gas sensor's impedance at elevated temperatures. The present invention is characterized in that the measured impedance values are used to control said sensor's operating temperature within a defined temperature range or to monitor said sensor's operating temperature via impedance monitoring.

17 Claims, 8 Drawing Sheets

PRIOR ART

| O2 Applied % | Sensor Output mV | O2 Measured % | Error O2 % |
|---|---|---|---|
| 11.7 | 3.98 | 11.61 | 0.09 |
| 1.32 | 33.44 | 1.27 | 0.05 |
| 0.1 | 67.41 | 0.10 | 0.00 |
| 8.32 | 8.41 | 8.32 | 0.00 |
| 6.5 | 11.53 | 6.58 | 0.08 |
| 0.5 | 44.7 | 0.54 | 0.04 |
| 0.4 | 49.3 | 0.39 | 0.01 |

FIG 8

METHOD OF SENSOR CONDITIONING FOR IMPROVING SIGNAL OUTPUT STABILITY FOR MIXED GAS MEASUREMENTS

RELATED APPLICATIONS

The present invention claims the benefit of U.S. Provisional Patent Application No. 61/545,613 filed on Oct. 10, 2011. The present invention also is a Continuation-in-Part of U.S. Ser. No. 11/152,971, filed Jun. 15, 2005, which claimed the benefit of U.S. Provisional Patent No. 60/580,606, filed on Jun. 18, 2004, and U.S. Provisional Patent No. 60/599,513, filed on Aug. 9, 2004. This invention incorporates by reference all the subject matter of the related applications as if it is fully rewritten herein.

BACKGROUND OF THE INVENTION

1. Field of the Invention

The present invention relates generally to an improvement in the present inventor's method or technique, as claimed in the related art, of conditioning a gas sensor through the application of pulse discharges in order to condition mixed-potential gas sensors for detecting gases commonly found in combustion exhaust.

2. Description of the Related Art

The sensing element used in zirconia oxygen sensors is generally formed of a zirconia thimble having an inner and outer metal coating, usually platinum, to form an electrode. The electrode is then used to measure the differential oxygen concentration between the measured gas on the outside of the thimble, and a reference gas, usually atmospheric, on the inside of the thimble. By measuring the voltage between two electrodes, the differential oxygen concentration can be calculated.

Solid electrolyte oxygen sensors comprising of gas impermeable zirconia ceramic separating two conductive (Pt) electrodes are widely used for combustion control in power plants as well as in the exhaust of automotive internal combustion engines. For utilization of oxygen sensors for industrial combustion control, the sensor must demonstrate certain performance criteria, i.e. a typical relative accuracy of between 3-5% (or absolute accuracy of 0.1-0.2%), a response time of less than 10 seconds, and a life expectancy typically greater than 1 year.

Figure 1:
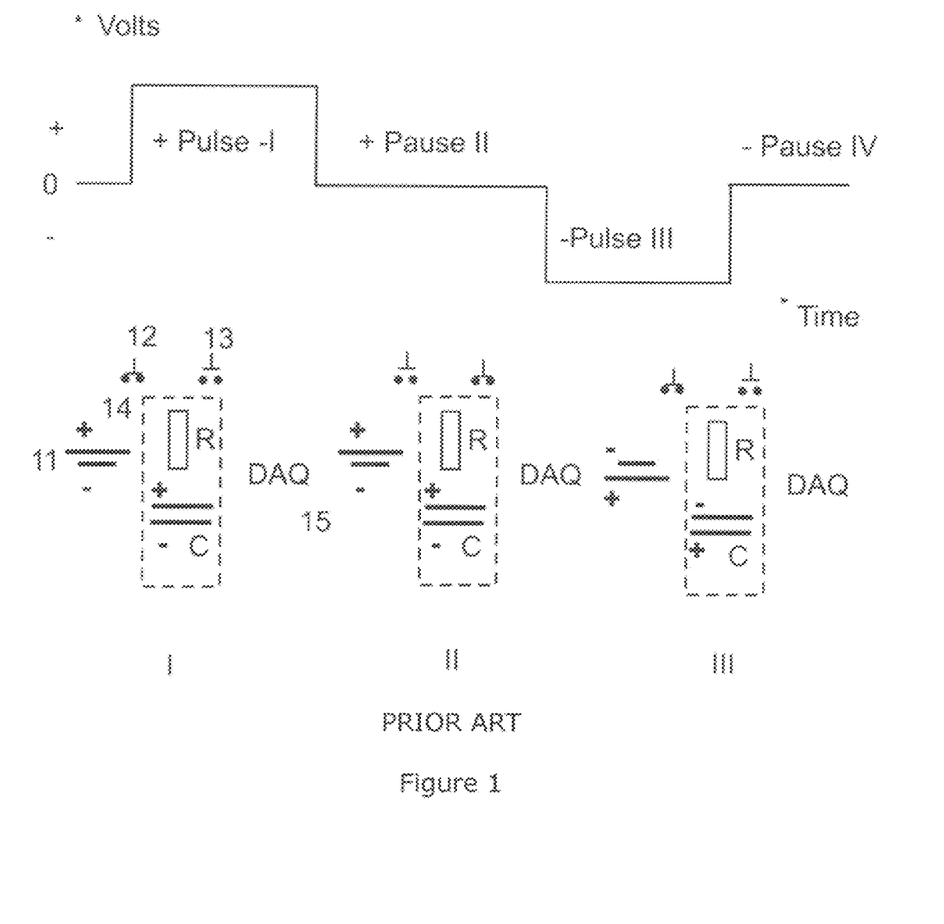
FIG. 1 is a schematic representation of the sensor conditioning in accordance with the PRIOR ART.
Figure 2:
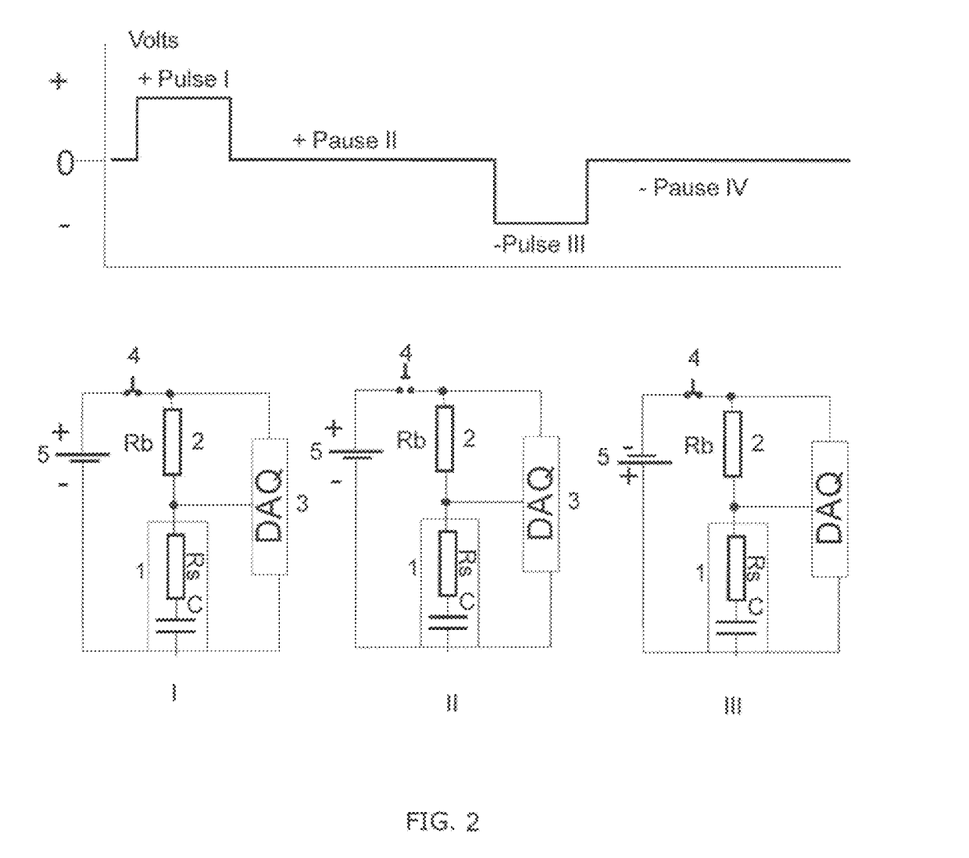
FIG. 2 is a suggested improved diagram according to an exemplary embodiment of the present invention in which the suggested improvements constitute a placement of an additional known resistor 2 (Rb) in series with the gas sensor and the controller 9 to applied regulated current to the internal heater of the sensor 8.

An improved method for activating such sensors is described in the inventor's own related prior art reflected in U.S. Pat. No. 7,585,402 and in the subsequent Continuation-in-Part of U.S. Ser. No. 11/152,971, filed Jun. 15, 2005 and still pending. A typical Schematic of the Pulse discharge technique is shown in FIG. 1 below, which is a representation of the sensor conditioning in accordance with the previous invention.

Sensors made with the inventor's own activation method result in numerous improvements in performance. Not only can such thimble sensors be used competitively with planar type designs as oxygen sensors, they can also be used as mixed potential sensors for the direct measurement of $NO_x$ and $O_2$ consecutively with the same sensor electrode. While this dual function of a mix potential sensor can have those benefits described in the related art over planar type $O_2$ sensors for current automotive applications (i.e. Exhaust Gas Oxygen (EGO)), it has been found that the mechanical stability of thimble type sensors and the stability of the sensor readings exceed performance of the planar sensors. Given that the stability of these planar sensors and their outputs are adversely affected by moisture, they can be used only in high dew point environments. While planar type sensors generally incorporate a heating element at the sensor surface so that the sensor surface temperature is known or controlled, the variation in the three dimensional geometry of thimble type sensors make such a solution unpractical.

Consequently, in order to obtain the benefits of stable sensor operation and high resolution at very low analyte concentrations it would be beneficial to be able to measure when the sensor impedance is within a proper range, and preferably to control the sensor impedance to within such a proper range.

SUMMARY OF THE INVENTION

An improvement to the pulse discharge technique is suggested by continuously measuring gas sensor impedance (resistance) at elevated temperatures. Measured impedance values are used to control sensor operating temperature within a defined temperature range by using internal heater of the standard heated EGO sensor or to monitor sensor operating temperatures via impedance monitoring. Suggested improvements provide for and allow the utilization of a lambda sensor as a wide band sensor in combustion exhaust without the need for a thermocouple mounted in direct proximity to the sensor's position through controlling of the impedance to within operational parameters.

Additional improvements are suggested to utilize lambda sensor for combined measurements of NOx, CO and Oxygen.

Additional improvements provide the measuring of sensor impedance by applying an alternating current (AC) sine wave between the sensor electrodes. This utilizes a lambda sensor for practical and accurate $O_2$ measurements. In alternate applications, the alternating current (AC) sign wave can be replaced with positive and negative direct current (DC) pulse waves to achieve a similar result.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the FIGS. 2-8, in which improvements to the pulse discharge technique are suggested by continuously measuring gas sensor impedance (resistance) at elevated temperatures. Measured impedance values are used to control sensor operating temperature within a defined temperature range or to monitor sensor operating temperatures via impedance monitoring.

Suggested improvements allow utilization of lambda sensor as a wide band sensor in combustion exhaust without necessity for a thermocouple mounted in direct proximity of the sensor position.

Additional improvements provide utilizing a lambda sensor for combined measurements of NOx, CO and $O_2$. Voltage drop is continuously measured on a known resistor during the charging phases of the process (phase I and III) with a data acquisition system. By dividing voltage over said known resistor value a charging current can be calculated. Voltage drop between the sensor electrodes is also measured during the charging phases of the process with a data acquisition system.

Figure 3:
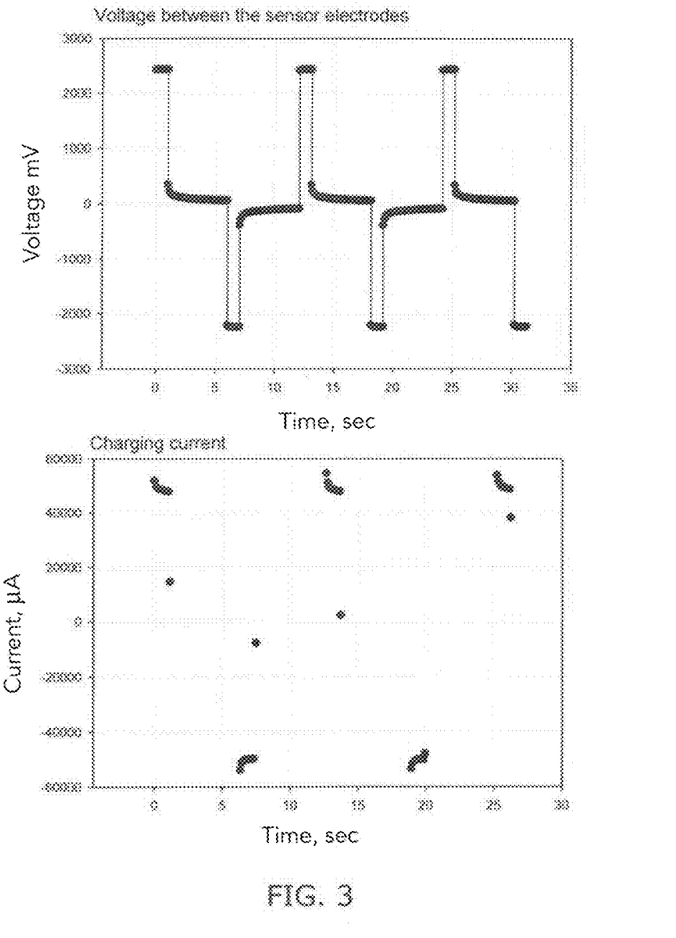
FIG. 3 is Voltage between the sensor electrodes and the charging current.
Figure 4:
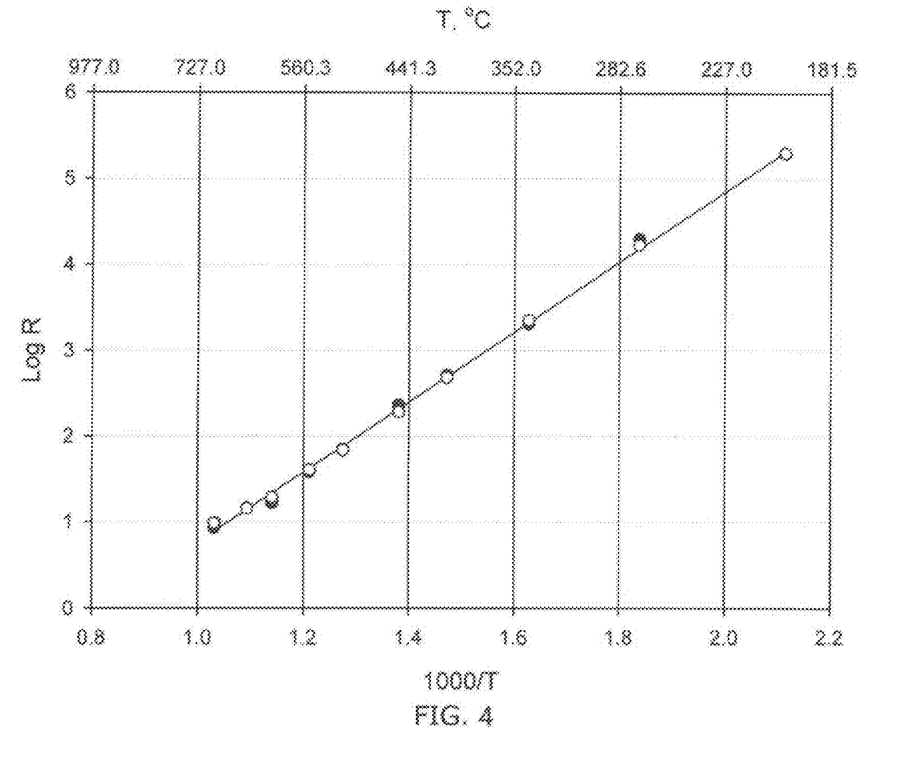
FIG. 4 is a Calibration curve for the sensor resistance versus temperature.

Measured curves of the charging current and voltage between the sensor electrodes are shown in FIG. 3. A measured voltage between two sensor electrodes is obtained. This measured voltage is divided by the measured current. The result of this division determines and provides the sensor impedance.

Sensor impedance is directly related to the sensor operating temperature. By positioning a ceramic measurement cell of the lambda sensor in an external furnace and monitoring said furnace and its cell temperature with an external thermocouple positioned in a direct proximity of the sensor element, a calibration curve establishing relations between the sensor impedance and its operating temperature is found (see FIG. 4).

Figure 5:
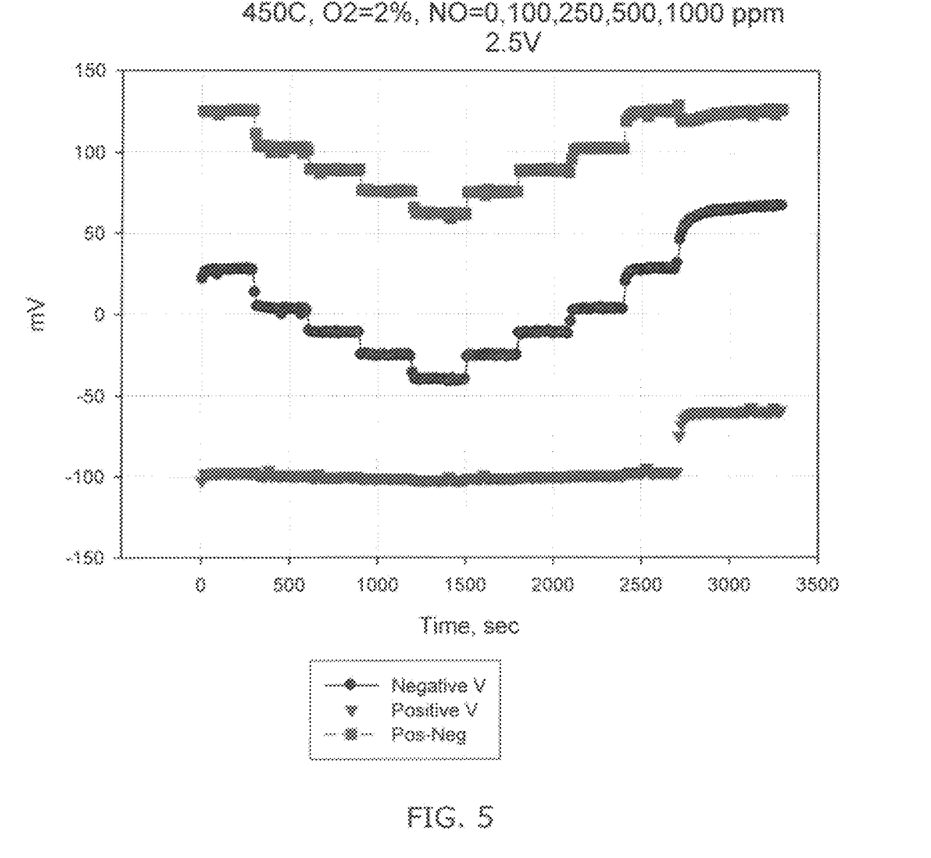
FIG. 5 is a Lambda sensor response to varying concentrations of NO.
Figure 6:
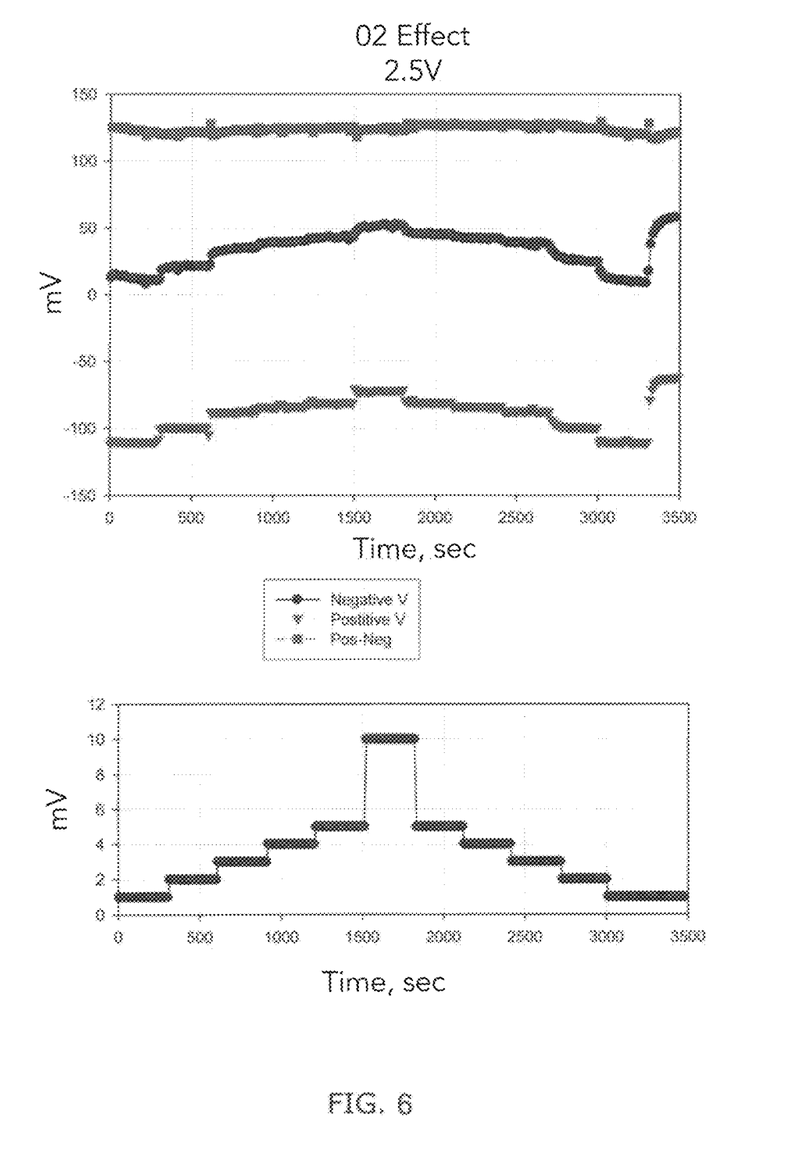
FIG. 6 is Lambda sensor response to varying concentrations of Oxygen at NO=0 ppm.

FIG. 5 shows a lambda sensor response to the pulse discharge technique at a constant oxygen concentration of 2% for different levels of NO. FIG. 6 shows sensor response to varying concentration on oxygen under at NO=0.

Figure 7:
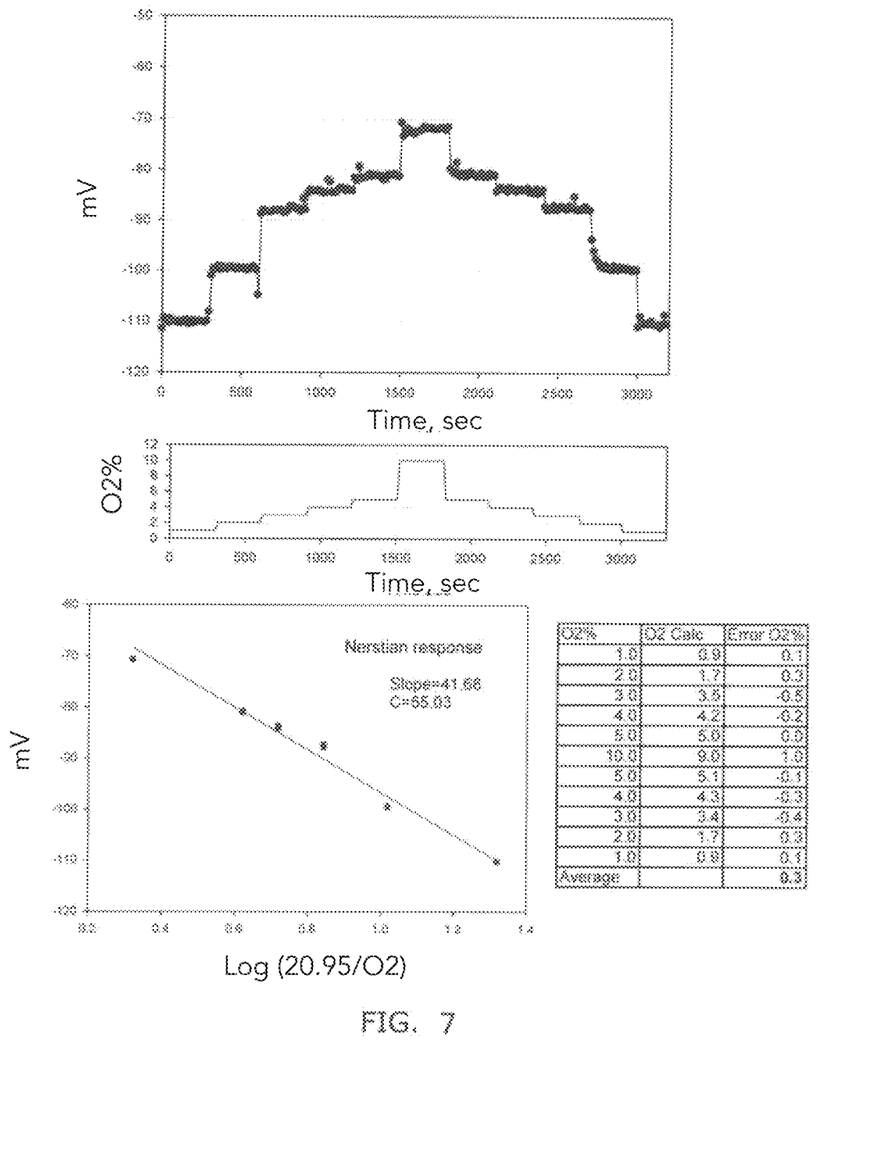
FIG. 7 is a Sensor calibration to Oxygen concentration measurements by using sensor response to positive voltage applied to the measurement electrode.

When negative voltage is applied to the measurement electrode (Phase III in the diagram), the sensor response is only sensitive to NO and not to $O_2$. Alternatively, when positive voltage is applied to the measurement electrode, the sensor response does not have NO sensitivity and is only sensitive to $O_2$. Combined measurements of NO and $O_2$, are possible as seen in FIG. 7.

By subtracting the negative voltage from the positive voltage (Vpos-Vneg), a pure NO response can be measured. When using Vpos response, the $O_2$ concentration can be measured.

Figure 8:
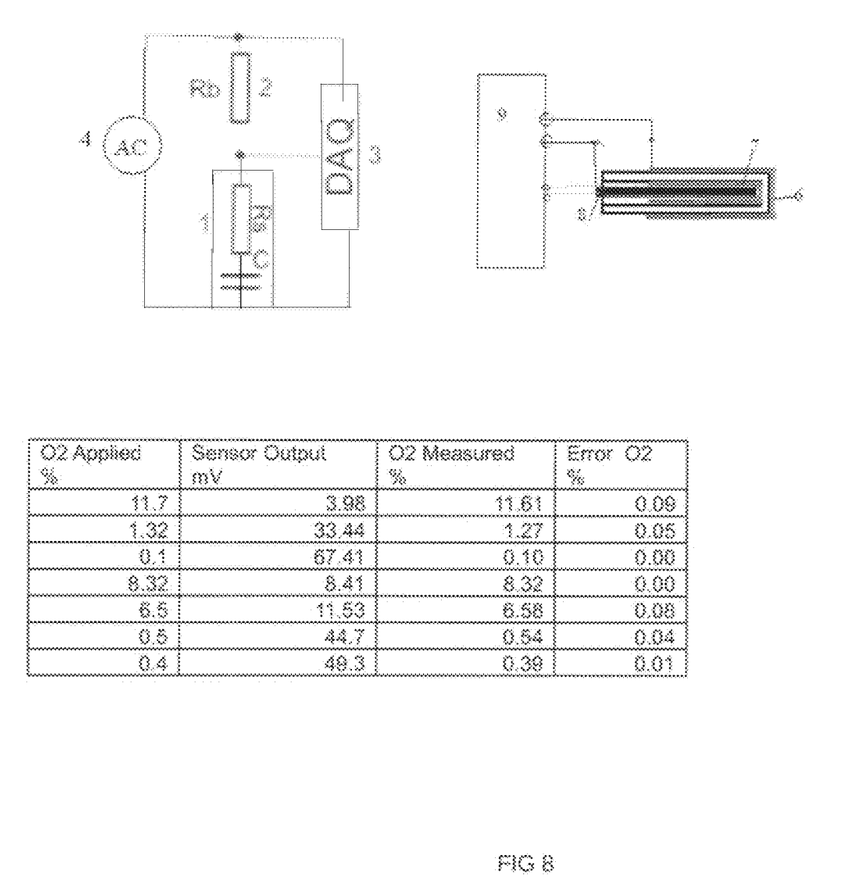
FIG. 8 describes Utilization of Lambda sensor as a wide band O2 sensor by measuring and controlling sensor impedance and measuring lambda sensor output for varying concentrations of measured O2.

Additional improvements provide the measuring of sensor impedance by applying an alternating current (AC) sine wave with the known frequency of ~10 Hz between the sensor electrodes and measuring the voltage on a known resistor Rb connected in series with the sensor. FIG. 8 shows results of O2 measurements in the range of 0.1-12% by measuring and controlling sensor impedance equal to ~200 Ohms. Sensor output to the varying concentrations of O2 was measured by decoupling of AC and DC signals. This utilizes a lambda sensor for practical and accurate $O_2$ measurements.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

What is claimed is:

1. An improved pulse discharge technique comprising:
   utilizing a lambda sensor adapted to be a potentiometric oxygen sensor in a combustion exhaust stream without the need for a thermocouple mounted in direct proximity of said lambda sensor's position;
   utilizing said lambda sensor for combined measurements of NOx, CO and $O_2$ by measuring sensor resistance via applying external DC voltage during a charging phase;
   measuring voltage drop continuously over known resistor during a charging phase and at elevated temperatures characterized in that the measured resistance values are used to control said sensor's operating temperature within a defined temperature range or to monitor said sensor's operating temperature via resistance monitoring; and
   measuring sensor resistance by applying a current sine wave between said sensor's electrodes.

2. The improved pulse discharge technique of claim 1, wherein said technique provides positioning a ceramic measurement cell of said lambda sensor in an external furnace and monitoring said furnace and its cell temperature with an external thermocouple positioned in a direct proximity of said sensor's element, yielding a calibration curve establishing relations between the sensor impedance and its operating temperature.

3. A method for controlling the operating characteristics of a gas sensor having at least one member of a thimble shaped solid state ionic conductor supporting at least one pair of metal electrodes and an internal heater, wherein said method comprising:
   a. heating the gas sensor to an elevated temperature by applying current to the internal heater;
   b. continuously measuring the gas sensor's resistance at said elevated temperature; and
   c. monitoring said measured resistance and controlling said sensor's operating temperature within a defined temperature range by controlling current through said internal heater.

4. The method for controlling the operating characteristics of a gas sensor of claim 3, wherein said sensor comprises a potentiometric oxygen sensor.

5. The method for controlling the operating characteristics of a gas sensor of claim 4, wherein said sensor comprises a lambda sensor.

6. The method for controlling the operating characteristics of a gas sensor of claim 5, wherein said lambda sensor is further adapted for combined measurements of NOx, CO and $O_2$, and wherein said method further comprises:
   d. continuously measuring voltage drop on a known resistance during a steps a. and step b. with a data acquisition system.

7. A method for controlling the operating characteristics of a gas sensor having at least one member of a thimble shaped solid state ionic conductor supporting at least one pair of metal electrodes and an internal heater, wherein said method comprising:
   a. heating the gas sensor to an elevated temperature by applying current to the internal heater;
   b. continuously measuring the gas sensor's impedance at said elevated temperature; and c. monitoring said measured impedance and controlling said sensor's operating temperature within a defined temperature range by controlling current through said internal heater;

wherein said continuously measuring the gas sensor's impedance is performed by applying a sine wave external voltage between said sensor's electrodes, measuring the voltage drop on a known resistor connected in series with the sensor, and extracting sensor response to the analyte gas by decoupling DC from AC signal.

8. An improved pulse discharge technique comprising continuously measuring a gas sensor's impedance at elevated temperatures characterized in that the measured impedance values are used to control said sensor's operating temperature within a defined temperature range or to monitor said sensor's operating temperature via impedance monitoring.

9. The improved pulse discharge technique of claim 8, further characterized by utilizing a lambda sensor adapted to be a potentiometric oxygen sensor in a combustion exhaust stream without the need for a thermocouple mounted in direct proximity of said lambda sensor's position.

10. The improved pulse discharge technique of claim 9, further comprising utilizing said lambda sensor for combined measurements of NOx, CO and $O_2$;
wherein voltage drop is continuously measured on a known impedance during a charging phase of the process with a data acquisition system.

11. An improved pulse discharge technique comprising:
continuously measuring a gas sensor's impedance at elevated temperatures characterized in that the measured impedance values are used to control said sensor's operating temperature within a defined temperature range or to monitor said sensor's operating temperature via impedance monitoring;
utilizing a lambda sensor adapted to be a potentiometric oxygen sensor in a combustion exhaust stream without the need for a thermocouple mounted in direct proximity of said lambda sensor's position;
utilizing said lambda sensor for combined measurements of NOx, CO and $O_2$, wherein voltage drop is continuously measured on a known impedance during a charging phase of the process with a data acquisition system; and
measuring sensor impedance by applying a current sine wave between said sensor's electrodes.

12. The improved pulse discharge technique of claim 11, wherein said technique provides positioning a ceramic measurement cell of said lambda sensor in an external furnace and monitoring said furnace and its cell temperature with an external thermocouple positioned in a direct proximity of said sensor's element, yielding a calibration curve establishing relations between the sensor impedance and its operating temperature.

13. An improved pulse discharge technique comprising continuously measuring a gas sensor's impedance at elevated temperatures characterized in that the measured impedance values are used to control said sensor's operating temperature within a defined temperature range or to monitor said sensor's operating temperature via impedance monitoring.

14. The improved pulse discharge technique of claim 13, further characterized by utilizing a lambda sensor adapted to be a potentiometric oxygen sensor in a combustion exhaust stream without the need for a thermocouple mounted in direct proximity of said lambda sensor's position.

15. The improved pulse discharge technique of claim 14, further comprising utilizing said lambda sensor for combined measurements of NOx, CO and $O_2$;
wherein voltage drop is continuously measured on a known impedance during a charging phase of the process with a data acquisition system.

16. An improved pulse discharge technique comprising:
utilizing a lambda sensor adapted to be a potentiometric oxygen sensor in a combustion exhaust stream without the need for a thermocouple mounted in direct proximity of said lambda sensor's position;
utilizing said lambda sensor for combined measurements of NOx, CO and $O_2$;
wherein voltage drop is continuously measured on a known impedance during charging phases of the process with a data acquisition system;
continuously measuring said lambda sensor's impedance at elevated temperatures characterized in that the measured impedance values are used to control said sensor's operating temperature within a defined temperature range or to monitor said sensor's operating temperature via impedance monitoring; and
measuring sensor impedance by applying a current sine wave between said sensor's electrodes.

17. The improved pulse discharge technique of claim 16, wherein said technique provides positioning a ceramic measurement cell of said lambda sensor in an external furnace and monitoring said furnace and its cell temperature with an external thermocouple positioned in a direct proximity of said sensor's element, yielding a calibration curve establishing relations between the sensor impedance and its operating temperature.

\* \* \* \* \*